(12) United States Patent
Jackson

(10) Patent No.: US 8,814,913 B2
(45) Date of Patent: Aug. 26, 2014

(54) HELICAL GUIDE AND ADVANCEMENT FLANGE WITH BREAK-OFF EXTENSIONS

(71) Applicant: Roger P Jackson, Prairie Village, KS (US)

(72) Inventor: Roger P Jackson, Prairie Village, KS (US)

(*) Notice: Subject to any disclaimer, the term of this patent is extended or adjusted under 35 U.S.C. 154(b) by 0 days.

(21) Appl. No.: 14/016,457

(22) Filed: Sep. 3, 2013

(65) Prior Publication Data

US 2014/0005726 A1    Jan. 2, 2014

Related U.S. Application Data

(63) Continuation of application No. 11/268,200, filed on Nov. 7, 2005, now Pat. No. 8,523,913, which is a continuation-in-part of application No. 11/101,859, filed on Apr. 8, 2005, which is a continuation-in-part of application No. 10/831,919, filed on Apr. 26, 2004, now Pat. No. 8,273,109, which is a continuation-in-part of application No. 10/236,123, filed on Sep. 6, 2002, now Pat. No. 6,726,689.

(60) Provisional application No. 60/627,000, filed on Nov. 10, 2004.

(51) Int. Cl.
*A61B 17/70* (2006.01)

(52) U.S. Cl.
USPC .......................................................... 606/273

(58) Field of Classification Search
USPC .................... 606/246, 264–273, 279, 301
See application file for complete search history.

(56) References Cited

U.S. PATENT DOCUMENTS

| | | |
|---|---|---|
| D791,548 | 6/1905 | Fischer |
| 791,548 A | 6/1905 | Fischer |
| 1,300,275 A | 4/1919 | Johnson |
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,243,717 A | 5/1941 | Moreira |
| 2,295,314 A | 9/1942 | Whitney |
| 2,346,346 A | 4/1944 | Anderson |
| 2,362,999 A | 11/1944 | Elmer |
| 2,537,029 A | 8/1946 | Cambern |
| 2,445,978 A | 7/1948 | Stellin |

(Continued)

FOREIGN PATENT DOCUMENTS

| | | |
|---|---|---|
| DE | 3630863 | 3/1988 |
| DE | 373809 | 5/1989 |

(Continued)

OTHER PUBLICATIONS

Brochure of Tyco/Healthcare/Surgical Dynamics on Spiral Radius 90D, Publication Date: Sep. 2001, pp. 1-8.

(Continued)

*Primary Examiner* — Pedro Philogene
*Assistant Examiner* — David Comstock
(74) *Attorney, Agent, or Firm* — John C. McMahon

(57) ABSTRACT

A spinal fixation device combines an open-headed anchor member, such as a bone screw or a hook with spaced apart arms forming a rod receiving channel. The arms have break-off arm extensions that are broken-off or separated after the rod is clamped. The closure and inner surfaces of the arms and tabs have mating helical anti-splay guide and advancement flanges formed thereon which radially interlock and mechanically cooperate to prevent splaying the arms and extensions as the closure is advanced into the rod receiving channel.

21 Claims, 4 Drawing Sheets

(56) References Cited

U.S. PATENT DOCUMENTS

| | | |
|---|---|---|
| 2,531,892 A | 11/1950 | Reese |
| 2,531,896 A | 11/1950 | Reese |
| 2,532,815 A | 12/1950 | Kindsvatter |
| 2,553,337 A | 5/1951 | Shafer |
| 2,778,265 A | 1/1957 | Brown |
| 2,813,450 A | 11/1957 | Dzus |
| 2,969,250 A | 1/1959 | Kull |
| 2,877,681 A | 3/1959 | Brown |
| 2,927,332 A | 3/1960 | Moore |
| 3,013,244 A | 12/1961 | Rudy |
| 3,143,029 A | 8/1964 | Brown |
| D200,217 S | 2/1965 | Curtiss |
| 3,236,275 A | 2/1966 | Smith |
| 3,370,341 A | 2/1968 | Allsop |
| 3,498,174 A | 3/1970 | Schuster et al. |
| 3,584,667 A | 6/1971 | Reiland |
| 3,604,487 A | 9/1971 | Gilbert |
| 3,640,416 A | 2/1972 | Temple |
| 3,812,757 A | 5/1974 | Reiland |
| 3,963,322 A | 6/1976 | Cryctko |
| 4,033,139 A | 7/1977 | Frederick |
| 4,041,939 A | 8/1977 | Hall |
| 4,103,422 A | 8/1978 | Weiss |
| 4,269,246 A | 5/1981 | Larson et al. |
| 4,369,769 A | 1/1983 | Edwards |
| 4,373,754 A | 2/1983 | Bollfrass et al. |
| 4,448,191 A | 5/1984 | Rodnyansky et al. |
| 4,484,570 A | 11/1984 | Sutter et al. |
| 4,492,500 A | 1/1985 | Ewing |
| 4,506,917 A | 3/1985 | Hansen Arne |
| 4,577,448 A | 3/1986 | Howorth |
| 4,600,224 A | 7/1986 | Blose |
| 4,641,636 A | 2/1987 | Cotrel |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,850,775 A | 7/1989 | Lee |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,022,791 A | 6/1991 | Isler |
| 5,026,373 A | 6/1991 | Ray et al. |
| 5,034,011 A | 7/1991 | Howland |
| 5,056,492 A | 10/1991 | Banse |
| 5,067,955 A | 11/1991 | Cotrel |
| 5,073,074 A | 12/1991 | Corrigan et al. |
| 5,092,635 A | 3/1992 | DeLange et al. |
| 5,102,412 A | 4/1992 | Rogozinski |
| 5,129,388 A | 7/1992 | Vignaud et al. |
| 5,129,899 A | 7/1992 | Small et al. |
| 5,147,360 A | 9/1992 | Dubousset |
| 5,147,363 A | 9/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,707 A | 2/1994 | Palm |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,375,823 A | 12/1994 | Navas |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,551 A | 12/1995 | Finn et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,507,745 A | 4/1996 | Logroscino et al. |
| 5,507,747 A | 4/1996 | Yuan et al. |
| 5,540,688 A | 7/1996 | Navas |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,605,458 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,624,442 A | 4/1997 | Mellinger et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,711,709 A | 1/1998 | McCoy |
| 5,713,705 A | 2/1998 | Grunbichler |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |

(56) References Cited

U.S. PATENT DOCUMENTS

| | | |
|---|---|---|
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| RE36,221 E | 6/1999 | Breard et al. |
| 5,910,142 A | 6/1999 | Tatar |
| 5,938,663 A | 8/1999 | Petreto |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,056,753 A | 5/2000 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,550 A | 10/2000 | Michelson |
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,186,718 B1 | 2/2001 | Fogard |
| 6,187,005 B1 | 2/2001 | Brace et al. |
| 6,193,719 B1 | 2/2001 | Gournay et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,241,730 B1 | 6/2001 | Alby |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,322,108 B1 | 11/2001 | Riesselmann et al. |
| 6,331,179 B1 | 12/2001 | Freid et al. |
| 6,349,794 B2 | 2/2002 | Spencer |
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,371,957 B1 | 4/2002 | Amrein et al. |
| 6,375,657 B1 | 4/2002 | Doubler et al. |
| 6,402,752 B2 | 6/2002 | Schaffler-Wachter et al. |
| 6,402,757 B1 | 6/2002 | Moore et al. |
| 6,432,109 B1 | 8/2002 | Letendart et al. |
| 6,440,135 B2 | 8/2002 | Orgay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,692,500 B2 | 2/2004 | Reed |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |

(56) References Cited

U.S. PATENT DOCUMENTS

| | | | |
|---|---|---|---|
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,207,992 B2 | 4/2007 | Ritland |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,127 B2 | 11/2007 | Leung et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 | 5/2009 | Biedermann et al. |
| 7,559,943 B2 | 7/2009 | Mujwid |
| 7,563,264 B2 | 7/2009 | Landry et al. |
| 7,563,275 B2 | 7/2009 | Falahee et al. |
| 7,569,061 B2 | 8/2009 | Colleran |
| 7,569,068 B2 | 8/2009 | Ramare |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,641,674 B2 | 1/2010 | Young |
| 7,645,294 B2 | 1/2010 | Kalfas et al. |
| 7,648,522 B2 | 1/2010 | David |
| 2001/0001119 A1 | 5/2001 | Lombardo |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0133159 A1 | 9/2002 | Jackson |
| 2002/0138076 A1 | 9/2002 | Biedermann et al. |
| 2002/0143341 A1 | 10/2002 | Biedermann |
| 2002/0173789 A1 | 11/2002 | Howland |
| 2002/0193795 A1 | 12/2002 | Gertzbein et al. |
| 2003/0004512 A1 | 1/2003 | Farris et al. |
| 2003/0022063 A1 | 1/2003 | Paulsen et al. |
| 2003/0023240 A1 | 1/2003 | Amrein et al. |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |

(56) References Cited

U.S. PATENT DOCUMENTS

| | | |
|---|---|---|
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0153068 A1 | 8/2004 | Janowski |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049589 A1 | 3/2005 | Jackson |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Jahng |
| 2005/0070899 A1 | 3/2005 | Doubler et al. |
| 2005/0080415 A1 | 4/2005 | Keyer et al. |
| 2005/0085812 A1 | 4/2005 | Sherman et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biederman et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228379 A1 | 10/2005 | Jackson |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0260058 A1 | 11/2005 | Cassagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Liebermann |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0025771 A1 | 2/2006 | Jackson |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |

(56) References Cited

U.S. PATENT DOCUMENTS

| | | |
|---|---|---|
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0100621 A1 | 5/2006 | Jackson |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0116677 A1 | 6/2006 | Burd et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195098 A1 | 8/2006 | Schumacher |
| 2006/0200128 A1 | 9/2006 | Mueller |
| 2006/0200130 A1 | 9/2006 | Hawkins |
| 2006/0200131 A1 | 9/2006 | Chao et al. |
| 2006/0200149 A1 | 9/2006 | Hoy et al. |
| 2006/0212033 A1 | 9/2006 | Rothman |
| 2006/0212034 A1 | 9/2006 | Triplett et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon et al. |
| 2006/0264933 A1 | 11/2006 | Baker et al. |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmannt |
| 2006/0271051 A1 | 11/2006 | Berrevoets et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016193 A1 | 1/2007 | Ritland |
| 2007/0016198 A1 | 1/2007 | Boehm, Jr. et al. |
| 2007/0016200 A1 | 1/2007 | Jackson |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073291 A1 | 3/2007 | Cordaro et al. |
| 2007/0073293 A1 | 3/2007 | Martz |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan et al. |
| 2007/0093814 A1 | 4/2007 | Callahan, II et al. |

(56) References Cited

U.S. PATENT DOCUMENTS

| | | |
|---|---|---|
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0260246 A1 | 11/2007 | Biedermann |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270815 A1 | 11/2007 | Johnson et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270839 A1 | 11/2007 | Jeon et al. |
| 2007/0288004 A1 | 12/2007 | Alvarez |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021462 A1 | 1/2008 | Trieu |
| 2008/0021464 A1 | 1/2008 | Morin et al. |
| 2008/0021473 A1 | 1/2008 | Butler et al. |
| 2008/0027432 A1 | 1/2008 | Strauss et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0058811 A1 | 3/2008 | Alleyne et al. |
| 2008/0058812 A1 | 3/2008 | Zehnder |
| 2008/0065073 A1 | 3/2008 | Perriello et al. |
| 2008/0065075 A1 | 3/2008 | Dant |
| 2008/0065077 A1 | 3/2008 | Ferree |
| 2008/0071273 A1 | 3/2008 | Hawkes et al. |
| 2008/0071274 A1 | 3/2008 | Enisgn |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0119858 A1 | 5/2008 | Potash |
| 2008/0140075 A1 | 6/2008 | Ensign et al. |
| 2008/0161859 A1 | 7/2008 | Nilsson |
| 2008/0161863 A1 | 7/2008 | Arnold et al. |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0195159 A1 | 8/2008 | Kloss et al. |
| 2008/0200956 A1 | 8/2008 | Beckwith et al. |
| 2008/0215095 A1 | 9/2008 | Biedermann et al. |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0249570 A1 | 10/2008 | Carson et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1 | 10/2008 | Garamszegi |
| 2008/0287994 A1 | 11/2008 | Perez-Cruet et al. |
| 2008/0288002 A1 | 11/2008 | Crall et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Battlers et al. |
| 2008/0312701 A1 | 12/2008 | Batters et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |

(56) References Cited

U.S. PATENT DOCUMENTS

| | | |
|---|---|---|
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |
| 2009/0131983 A1 | 5/2009 | Biedermann |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0256684 A1 | 10/2010 | Seme et al. |

FOREIGN PATENT DOCUMENTS

| | | |
|---|---|---|
| DE | 9202745 | 4/1992 |
| DE | 4425392 | 11/1995 |
| DE | 19507141 | 9/1996 |
| DE | 19509331 | 9/1996 |
| DE | 29806563 | 7/1998 |
| DE | 28910798 | 12/1999 |
| DE | 29810798 | 12/1999 |
| DE | 19951145 | 5/2001 |
| DE | 10157969 | 2/2003 |
| EP | 0195455 | 9/1986 |
| EP | 0172130 | 2/1987 |
| EP | 0276153 | 7/1988 |
| EP | 0465158 | 1/1992 |
| EP | 0667127 | 8/1995 |
| EP | 0677277 | 10/1995 |
| EP | 0885598 | 12/1998 |
| EP | 1090595 | 4/2001 |
| EP | 1121902 | 8/2001 |
| EP | 1190678 | 3/2002 |
| EP | 1210914 | 6/2002 |
| EP | 1277444 | 1/2003 |
| EP | 1449486 | 8/2004 |
| EP | 1570795 | 9/2005 |
| EP | 1579816 | 9/2005 |
| EP | 1634537 | 3/2006 |
| EP | 1925263 | 5/2008 |
| FR | 2467312 | 4/1981 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 203508 | 9/1923 |
| GB | 2082709 | 3/1982 |
| GB | 2140523 | 11/1984 |
| GB | 9202745.8 | 4/1992 |
| GB | 2365345 | 2/2002 |
| GB | 2382304 | 5/2003 |
| JP | 9-504727 | 5/1997 |
| JP | 2000325358 | 11/2000 |
| RU | 371359 | 2/1993 |
| SU | 371359 | 8/1973 |
| WO | WO92/03100 | 3/1992 |
| WO | WO94/10927 | 5/1994 |
| WO | WO94/10944 | 5/1994 |
| WO | WO94/26191 | 11/1994 |
| WO | WO95/01132 | 1/1995 |
| WO | WO95/35067 | 12/1995 |
| WO | WO96/06576 | 3/1996 |
| WO | WO96/28118 | 9/1996 |
| WO | WO97/14366 | 4/1997 |
| WO | WO98/32386 | 7/1998 |
| WO | WO01/45576 | 6/2001 |
| WO | WO01/49191 | 7/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/021900 | 3/2004 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/119241 | 11/2006 |
| WO | WO2007/118045 | 10/2007 |
| WO | WO2007/124222 | 11/2007 |
| WO | WO2007/124249 | 11/2007 |
| WO | WO2007/130835 | 11/2007 |
| WO | WO2007/130840 | 11/2007 |
| WO | WO2007/130941 | 11/2007 |
| WO | WO2008/088731 | 7/2008 |
| WO | WO2009/015100 | 1/2009 |

OTHER PUBLICATIONS

CD Horizon M8 Multi Axial Screw Spinal System Brochure, Medtronic SofamorDanek, no publish date.
Claris Instrumentation Brochure, G Med, pub. 1997.
Contour Spinal System Brochure, Ortho Development, no publish date.

(56) References Cited

OTHER PUBLICATIONS

EBI Omega 21 Brochure, EBI Spine Systems, pub. 1999.
SDRS Surgical Dynamics Rod System Brochure, Surgical Dynamics, pub. 1998-99.
Silhouette Spinal Fixation System Brochure, SulzerMedica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker HowmedicaOsteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker HowmedicaOsteonics, no publish date.

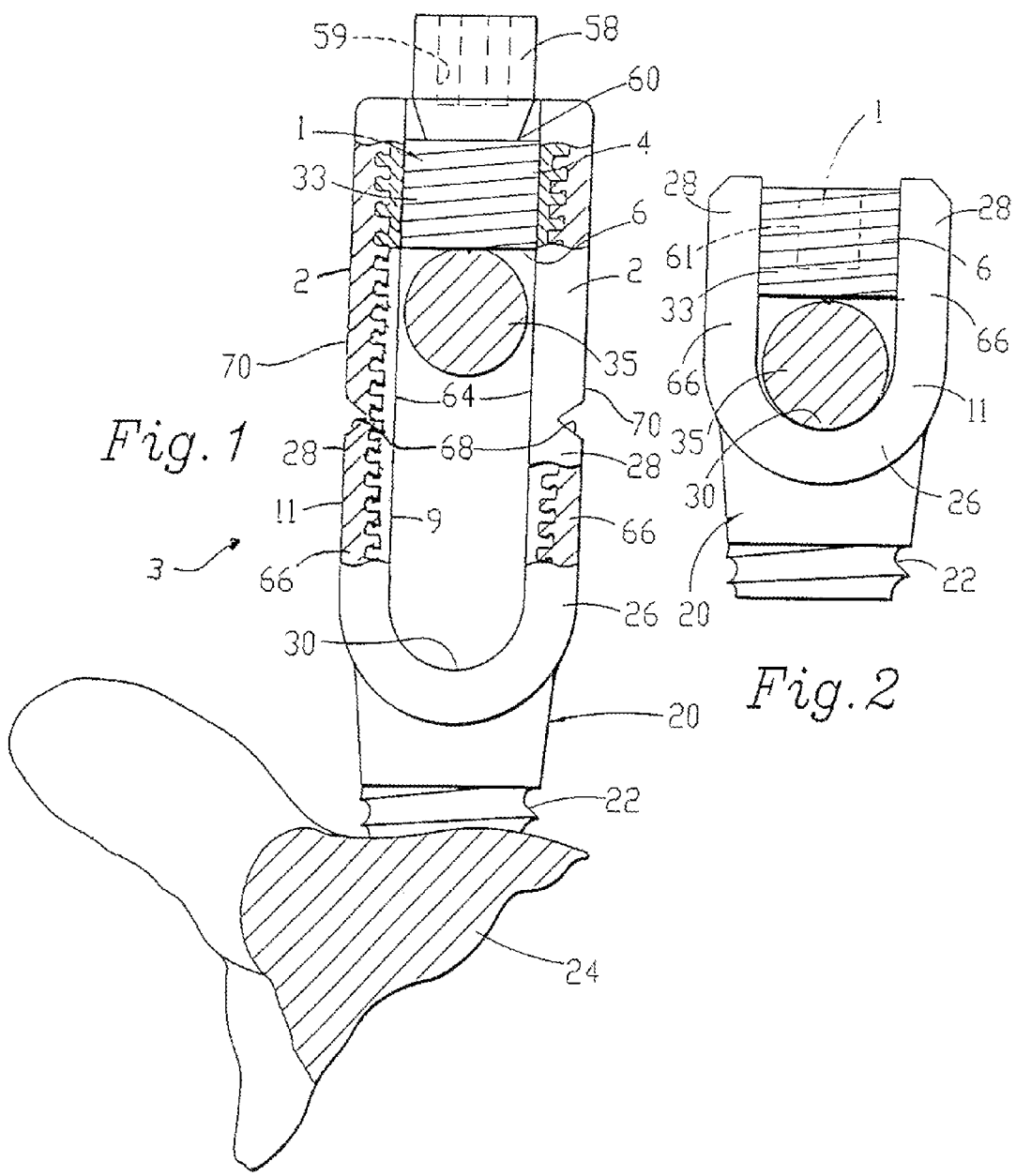

HELICAL GUIDE AND ADVANCEMENT FLANGE WITH BREAK-OFF EXTENSIONS

CROSS-REFERENCE TO RELATED APPLICATIONS

This application is a continuation of U.S. patent application Ser. No. 11/268,200, filed Nov. 7, 2005, now U.S. Pat. No. 8,523,913, which is incorporated herein by reference. U.S. patent application Ser. No. 11/268,200 claims the benefit of U.S. Provisional Application No. 60/627,000 filed Nov. 10, 2004 and is a continuation-in-part of U.S. patent application Ser. No. 11/101,859, filed Apr. 8, 2005 which is a continuation-in-part of U.S. patent application, Ser. No. 10/831,919 filed Apr. 26, 2004, which is a continuation-in-part of U.S. patent application Ser. No. 10/236,123 filed Sep. 6, 2002, now U.S. Pat. No. 6,726,689, all of which are incorporated herein by reference.

BACKGROUND OF THE INVENTION

The present invention relates to improvements in interlocking or interconnecting helical guide and advancement structures such as helical flanges and, more particularly, to mating helical flange arrangements having an anti-splay lip on one flange and a cooperating and interlocking anti-splay groove on the other flange, the flanges being configured so that when radial loading or engagement occurs, the lip and groove resist splaying of an outer one of the members having one of the cooperating flanges on it. Such flanges with anti-splay contours are particularly advantageous when used in combination with open headed bone screws formed with extended arms or tabs to facilitate the capture and reduction of spinal fixation rods, after which the arm extensions or tabs are broken off at weakened areas to form a low profile implant. In particular, in the present invention, the interlocking anti-splay components also are found on the extensions such that force can be applied to a closure and through the closure to a rod positioned between the extensions without splaying the extensions, as the closure holds them in fixed position relative to each other as the closure traverses between the extensions.

Medical implants present a number of problems to both surgeons installing implants and to engineers designing them. It is always desirable to have an implant that is strong and unlikely to fail or break during usage. Further, if one of a set of cooperating components is likely to fail during an implant procedure, it is desirable to control which particular component fails and the manner in which it fails, to avoid injury and to minimize surgery to replace or repair the failed component. It is also desirable for the implant to be as small and lightweight as possible so that it is less intrusive to the patient. These are normally conflicting goals, and often difficult to resolve.

One type of implant presents special problems. In particular, spinal anchor members such as bone screws, hooks, and the like are used in many types of back surgery for repair of problems and deformities of the spine due to injury, disease or congenital defect. For example, spinal bone screws typically have one end that threads into a vertebra and a head at an opposite end. The head is formed with an opening to receive a rod or rod-like member which is then both captured in the channel and locked in the head to prevent relative movement between the various elements subsequent to installation.

A particularly useful type of head for such bone screws is an open head wherein an open, generally U-shaped channel is formed in the head, and the rod is simply laid in the open channel. The channel is then closed with some type of a closure member which engages the walls or arms forming the head and clamps or secures the rod in place within the channel. While the open headed devices are often necessary and preferred for usage, there is a significant problem associated with them. The open headed devices conventionally have two upstanding arms that are on opposite sides of the channel that receives the rod member. The top of the channel is closed by a closure member after the rod member is placed in the channel. Many open headed implants are closed by threaded plugs that screw into threads formed on internal surfaces between the arms, because such configurations have low profiles.

However, such threaded plugs have encountered problems in that they produce radially outward forces that lead to splaying of the arms or at least do not prevent splaying that in turn may lead to loosening of parts and failure of the implant. In order to lock the rod member in place, a significant force must be exerted on the relatively small plug or on a set screw of some type. The forces are required to provide enough torque to insure that the rod member is clamped or locked securely in place relative to the bone screw, so that the rod does not move axially or rotationally therein. This typically requires torques on the order of 100 inch-pounds.

Because open headed implants such as bone screws, hooks and the like are relatively small, the arms that extend upwardly at the head can be spread by radially outwardly directed forces in response to the application of the substantial torquing force required to clamp the rod member. Historically, early closures were simple plugs that were threaded with V-shaped threads and which screwed into mating threads on the inside of each of the arms. The outward flexure of the arms of the head is caused by mutual camming action of the V-shaped threads of the plug and head as advancement of the plug is resisted by clamping engagement with the rod while rotational urging of the plug continues. If the arms are sufficiently spread, they can allow the threads to loosen or disengage and the closure to fail. To counter this, various engineering techniques were applied to the head to increase its resistance to the spreading force. For example, the arms were significantly strengthened by increasing the width of the arms by many times. This is undesirable as it leads to a larger profile implant, which is always undesirable and may limit the working space afforded to the surgeon during implant procedures. Alternatively, external caps were devised which engaged external surfaces of the head. In either case, the unfortunate effect was to substantially increase the bulk, size and profile of the implant, especially when external nuts are used which may take up enough space along the rod so as to leave too little space for all the implants needed.

The radial expansion problem of V-threads has been recognized in various other applications of threaded joints. To overcome this problem, so-called "buttress" threadforms were developed. In a buttress thread, the trailing or thrust surface, also known as the load flank, is oriented perpendicular to the thread axis, while the leading or clearance surface, also known as the stab flank, remains angled. This results in a neutral radial reaction of a threaded receptacle to torque on the threaded member received. However, even buttress threaded closures may fail as such do not structurally resist splaying of the arms.

Development of threadforms proceeded by applicant from buttress threadforms and square threadforms, which have a neutral radial effect on the screw receptacle, to reverse angled threadforms which can positively draw the threads of the receptacle radially inward toward the thread axis when the plug is torqued. In a reverse angle threadform, the trailing side of the external thread is angled toward the thread axis instead of away from the thread axis, as in conventional V-threads. However, outward radial forces on the arms at higher torques can lead to failure and positive mechanical interlocking between the arms and the closure is more desirable and secure. In the present application, such positive interlocking is also provided in vertical extensions of the arms that are eventually broken away and removed.

When rods are implanted in spinal fixation systems, it is often necessary to shape the rod in various ways to properly position vertebrae into which open headed bone screws and related implants have been implanted. The bone screw or implant heads are minimized in length to thereby reduce the profile and minimize the impact of the implanted system on the patient. However, it is often difficult to capture a portion of a straight or curved rod in a short implant head to clamp it within the arms. The extensions allow the arms to extend upwardly and capture the rod therebetween. In this way, the closure can be more easily inserted and rotated to drive the rod downwardly into the head of the implant.

SUMMARY OF THE INVENTION

The present invention provides improved mating guide and advancement flange structure for guiding and advancing an inner member into an outer member in response to relative rotation of the inner and outer member. The structure includes an inner flange on the inner member and an outer flange on the outer member which have complementary contours cooperating on engagement to helically guide the inner member into the outer member by relative rotation about a helical axis and which each radially interlock with opposite structure as the closure is rotated. The inner flange has a radially outward crest and a radially inward root. Conversely, the outer flange has a radially inward crest and a radially outward root.

Each of the inner and outer flange has respective stab flank on a leading side relative the direction of advancement of the inner member into the outer member and a respective load flank on the trailing side of the flange. At least one of the flanks on one member has anti-splay contours forming a lip or bead which projects axially and extends helically therealong, while a corresponding one of the flanks has anti-splay contours forming a complementary groove depressed in an axial direction and positioned to receive the lip. For example, if the lip is formed on the load flank of the inner member at its radial crest, the corresponding groove is formed into the load flank of the outer member near its root.

The lip and groove have radially oppositely facing anti-splay surfaces which are positioned to enable radial engagement or loading of the anti-splay surfaces to resist or prevent splaying of the outer member when the inner member is strongly torqued into the outer member. Preferably, the anti-splay surfaces on the inner member are continuous, whereas the outer member is divided into two parts which are spaced from one another and the anti-splay surfaces thereon are discontinuous.

In a first embodiment of the flange, a lip is formed on the load flank of the inner flange adjacent a crest of the flange. The lip has an anti-splay surface or shoulder which faces inwardly toward coincident helical axes of the inner and outer members which form a joint axis common to both members when so engaged. A corresponding groove is formed into the load flank of the outer flange near the root of the outer flange. The groove has an anti-splay surface or shoulder which faces outwardly away from the joint axis of the members. The anti-splay surfaces of the lip and groove are positioned to mutually engage in a radial direction to resist splaying of the outer member when the inner member is strongly torqued into the outer member.

In the first embodiment, the load flanks of the inner and outer flanges are angled in a slightly "positive" direction; that is, in cross section the load flanks form slightly obtuse angles with the joint axis of the members.

In embodiments wherein the inner and outer flanges have relatively equal cross sections with generally similar shapes, the outer flange tends to be somewhat stronger than the inner flange. As a result of this, when the inner member is very strongly torqued into the outer member, the inner flange is likely to fail before the outer flange.

Although the preceding description of the load flanges describes the load flank of the inner flange as having a lip and the load flank of the outer flange as having a groove, each load flank could be accurately described as having both a lip and a groove. The lip of the inner flange is defined by a radially inward groove while the groove formed in the outer flange defines a radially inward lip. In any case, the lip of one flange enters the groove of the other flange so that the anti-splay surfaces of the flanges are placed in mutually facing relation when the inner member is advanced into the outer member.

The present invention does not limit the anti-splay contours solely to the load flanks of the inner and outer flanges. There are advantages to be gained by forming the lips and grooves on the respective stab flanks of the inner and outer flanges, on leading sides of the flanges as the inner member is advanced into the outer member.

Although it is desirable to form the arms of an open-headed bone screw and related implants as short as possible to result in a low profile implant, it is often difficult to urge a spinal fixation rod into the U-shaped channel between the arms of such a bone screw head. In general, the rods are shaped to determine the shaped of the corrected curvature of the spinal column and are anchored along their length to open-headed bone screws implanted into individual vertebrae. Because of the complex curvature that must be applied to the rods, it is sometimes difficult to reduce a portion of such a rod toward a selected bone screw or implant in a vertebra with a conventionally formed open-head with spaced arms for receiving both the rod and a closure.

The present invention solves this problem by forming arm extensions or tabs on the screw head which are connected to main portions of the arms by weakened break regions. Inner surfaces of the extensions have the helical guide and advancement flanges formed thereon to receive a closure with a flange complementary to the flange of the arms of the screw head. In particular, the extensions have the same anti-splay structure thereon as is found on the arms and the structure on the extensions is aligned with that on the arms so as to provide a continuous helical path for the mating structure on the closure to follow. The extensions or tabs enable the rod to be captured at a greater distance from the anchoring vertebra and urged toward the vertebra by advancement of the closure toward the open head. When the rod has been seated in the rod receiving channel and in the head sufficiently clamped, the tabs can be broken off the main portions of the arms to provide the desired low profile implant. Just as the anti-splay guide and advancement structure on the closure and arms cooperate to prevent splaying of the arms, the anti-splay structure on the extensions cooperates with the cooperating structure on the closure to prevent unwanted splaying of the extension and guides the closure to allow mating with the guide and advancement structure on the arms simply by rotating the closure.

That is, the guide and advancement structure on the closure does not have to be realigned with the cooperating structure on the arms and pressure applied to the rod while between the extensions is continued as the rod passes between the arms.

The anti-splay lip and groove of the flanges of the present invention make the use of such extended arms or tabs possible, even when substantial force must be applied to the rod. This is a substantial improvement over use of V-threads that may cause outward splaying of the extensions as force is applied to the rod by the closure.

OBJECTS AND ADVANTAGES OF THE INVENTION

The principal objects of the present invention include: providing an improved helical guide and advancement flange structure for guiding and advancing an inner member into an outer member; providing such flange structure for cooperatively radially interlocking between a closure and both implant arms and extensions for such arms as a rod is passed between the extensions to the arms under pressure being applied by rotating or torquing the closure; providing, particularly, improvements in helical guide and advancement flanges incorporating radially loaded lip and groove contours; providing such flange structure wherein the outer member is subject to being splayed in reaction to advancement and torquing of the inner member within the outer member and wherein an inner flange of the inner member and an outer flange of the outer member are particularly configured to cooperate in such a manner as to radially interlock and resist such splaying while allowing rotation and axial advancement; providing such flange structure in which the inner and outer flanges are provided with contours including mutually facing surfaces which radially engage when the inner member is advanced into the outer member to resist splaying of the outer member; providing such flange structure in which anti-splay contours are formed on a trailing load flank of each flange to form an anti-splay lip near a crest region of the inner flange and a cooperating anti-splay groove near a root region of the outer flange; providing such flange structure in which the anti-splay contours are alternatively applied to a leading stab flank of each flange to form an anti-splay lip near a crest region of the inner flange and a cooperating anti-splay groove near a root region of the outer flange; providing such flange structure in which the anti-splay contours are alternatively formed on both the load and stab flanks of each flange to form anti-splay lips near a crest region of the inner flange and cooperating anti-splay grooves near a root region of the outer flange; providing such flange structure which is particularly well adapted for use in surgically implanted structure, such as spinal fixation hardware and, particularly, to receivers and cooperating closures which are used to receive and clamp spinal fixation rods; providing such flange structure which is particularly well adapted for use with open headed bone screws which have extended arms for facilitating the capture and reduction of spinal fixation rods and which are afterwards separated from the screw heads and related implants to provide low profile implants; and providing such improved helical guide and advancement flanges with radially loaded lips which are economical to manufacture, which are strong and effective in use, and which are particularly well adapted for their intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an enlarged fragmentary side elevational view of a spinal implant incorporating the helical guide and advancement flange on a closure with a radially loaded lip urging a rod between extensions of arms forming a rod receiving channel on a medical implant bone screw with portions broken away to show detail thereof.

FIG. 2 is a view similar to FIG. 1 and shows the implant with the closure clamping a spinal fixation rod within the channel with the extensions removed.

DETAILED DESCRIPTION OF THE INVENTION

Figure 3:
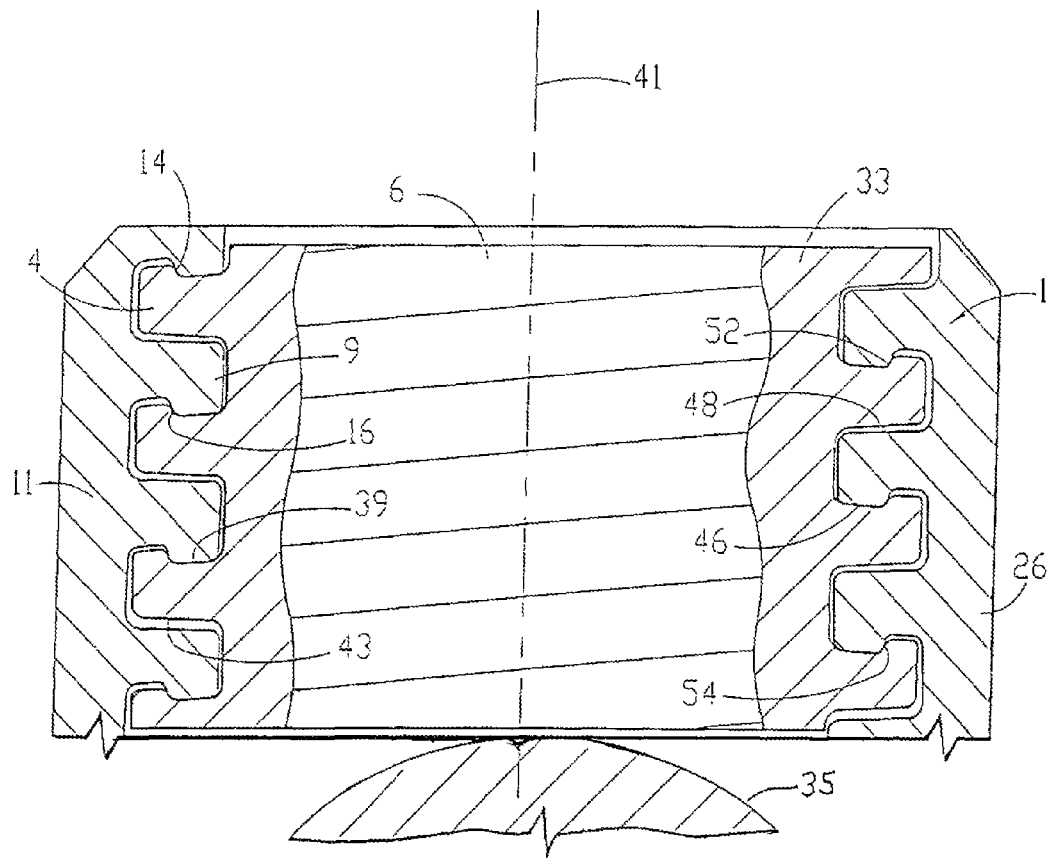
FIG. 3 is a greatly enlarged fragmentary sectional view at a right angle to the view shown in FIG. 2 and illustrates details of the cooperating flanges with the closure strongly torqued into the open headed screw.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a helical guide and advancement flange structure in combination with break-off tabs or extension 2 used in conjunction with a medical implant 3 which embodies the present invention.

The flange structure, or flange form, 1 generally includes an inner flange 4 (FIG. 3) extending helically on an inner member 6 and an outer flange 9 extending helically within an outer member 11. The flanges 4 and 9 cooperate to helically guide the inner member 6 into the outer member 11 when the inner member 6 is rotated and advanced into the outer member 11. The inner and outer flanges 4 and 9 have respective anti-splay contours 14 and 16 which cooperate to prevent splaying tendencies of the outer member 11 when the inner member 6 is strongly torqued therein.

In the illustrated embodiment the implant 3 comprises an open-headed bone screw 20 forming the outer member 11 thereon and having a threaded shank 22 adapted for threaded implanting into a bone, such as a vertebra 24. The bone screw 20 has a U-shaped open head 26 formed by spaced apart arms 28 defining a rod receiving channel 30 which is configured to receive a rod 35 and thereafter the rod is clamped or secured within the head 26 to thereby fix the position of the vertebra 24 relative to the rod 35.

The illustrated inner member 6 is a closure 33 which is helically advanced by rotation thereof into the head 26 of the screw 20 and torqued against the rod 35 to clamp the rod within the head 26. Although embodiments of the outer member 11 and inner member 6 are illustrated herein, as the screw head 26 and the closure 33, the flange structure 1 is not intended to be limited to such an application. It is especially noted that the implant 3 may be a hook or other implant structure having a rod receiving channel. Also, while the illustrated screw 20 is shown as a one-piece screw, it is intended that the flange structure 1 be adaptable for use with a polyaxial type of screw.

The inner flange 4 has a load flank 39 on a trailing side relative to a direction of advancement along a helical axis 41 (FIG. 3) and a stab flank 43 on an opposite leading side. Similarly, the outer flange 9 has a load flank 46 on a trailing side and a stab flank 48 on an opposite leading side. The load flanks 39 and 46 may also be referred to as thrust surfaces of the flanges 4 and 6, while the stab flanks 42 and 48 may also be referred to as clearance surfaces. In general, the load flanks 39 and 46 are positively engaged and axially loaded, that is loaded in the direction of the axis 41, when the inner member 6 is advanced into the outer member 11. As relative torque between the inner member 6 and the outer member 11 increases, by engagement with a clamped member such as the rod 35, there is a tendency for the arms 28 of the outer member 11, to splay outward away from the axis 41. In the flange structure 1 of the present invention, the inner and outer anti-splay contours 14 and 16 include respective anti-splay surfaces 52 and 54 which are mutually engaged in a radial direction to radically interconnect, to mechanically interlock and resist such splaying tendencies. Because of the anti-splay configuration of the flange structure 1, the relative torque between the inner and outer members 6 and 11 can be much higher in comparison to conventional V-threads or guide and advancement structures which do not have anti-splay contours, thereby allowing a considerably higher, more positive clamping force to be applied to the closure 33 and the rod 35.

Figure 4:
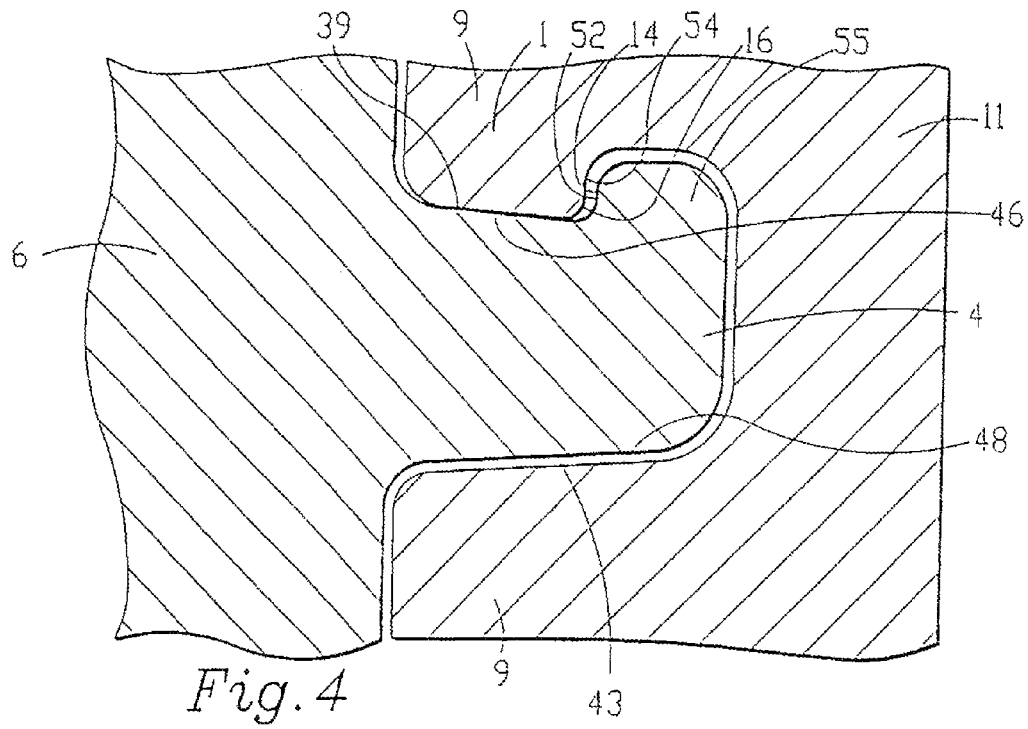
FIG. 4 is a further enlarged fragmentary sectional view of a preferred flange structure according to the present invention and illustrates an anti-splay lip on a load flank of an inner flange and an anti-splay groove on a load flank of an outer flange, the load flanks being parallel and somewhat positive in angular orientation relative to a helical axis.
Figure 5:
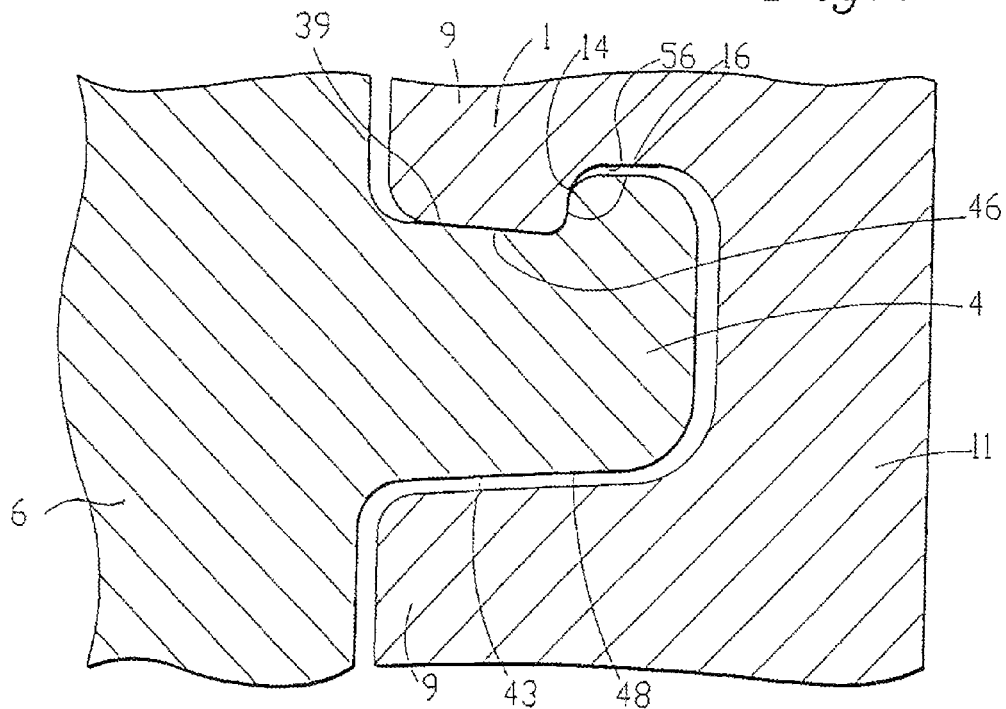
FIG. 5 is a view similar to FIG. 4 and illustrates the preferred flange structure with the inner member strongly torqued within the outer member, thereby mutually engaging the anti-splay surfaces of the lip and groove.

In the illustrated flange structure 1, the inner anti-splay surface 52 is formed by an anti-splay lip 55 extending axially from the load flank 39 of the inner flange 4. Similarly, the outer anti-splay surface 54 is formed by a groove 56 formed into the load flank 46 of the outer flange 9. The lip 55 and groove 56 are shaped in a complementary manner so that the lip 55 is received within the groove 56 when the inner member 6 is advanced into the outer member 11. Although FIGS. 3-5 illustrate a flange structure 1 of a particular configuration and contour, other configurations and contours are contemplated, as disclosed in Ser. No. 10/236,123 referenced above and enclosed herein by reference.

The closure 33 illustrated in FIG. 1 has a break-off installation head 58 which is provided with a non-round installation socket 59, such as a Torx shaped socket, a hexagonal Allen socket, or the like to receive an appropriately configured installation tool (not shown). The break-off head 58 is joined to the main body of the closure 33 by a weakened region 60 which is configured to limit the torque that can be applied to the head 58, relative to the closure 33, without the head separating from the closure 33 by failure of the weakened region 60. By this means, the head 58 separates from the closure 33 when a selected torque is reached in clamping the rod 35, to thereby provide a low profile implant. Alternatively, the closure 33 could be provided without the break-off head 58. The closure 33 has a non-round socket 61 (FIG. 2) to receive a tool to enable removal of the closure 33 from the screw head 26, if necessary. Such a socket 61 could also be employed for installation of the closure 33 into the screw head 26.

Referring particularly to FIG. 1, the bone screw 20 is provided with the arm tabs on extensions 2 to increase the initial length of the arms 28 and, thus, forming a rod receiving passageway between the extensions 2 and thereby increasing the length of the rod receiving channel 30 by the length of the passageway. The purpose for the lengthened channel 30 is to enable capture of the rod 35 within the channel 30 at a greater distance from the vertebra 24, whereby the rod 35 can be captured by the closure 33 and "reduced" or urged toward a seated position within the channel 30 by advancement of the closure 33. This provides effective leverage in reducing the position of the rod 35 or the vertebra itself. For this purpose, inner surfaces 64 of the tabs 2 are provided with the helical outer flange 9 which extends continuously from main portions 66 of the arms 28 and along the extensions 2 to form a continuous and uniform helical pathway therebetween.

The break-off extensions 2 are connected to the main portions 66 of the arms 28 by reduced or otherwise weakened regions 68. The bone screw 20 illustrated in FIG. 1 shows the weakened regions 68 as regions adjacent V-shaped notches formed into external surfaces 70 of the arms 28 which diminish the thickness of the material forming the arms 28. Alternatively, other shapes or configurations could be employed to form the weakened regions 68. The weakened regions 68 are strong enough to enable the rod 35 to be urged toward its seated position (FIG. 2). However, the extensions 2 can be broken off or separated from the main portions 66 of the arms 28 by pivoting or bending the extensions 2 back and forth about the regions 68 while the main portions 66 are held in place, after the closure 33 has passed between the extensions 2. The resulting low-profile implanted structure is shown in FIG. 2.

Figure 6:
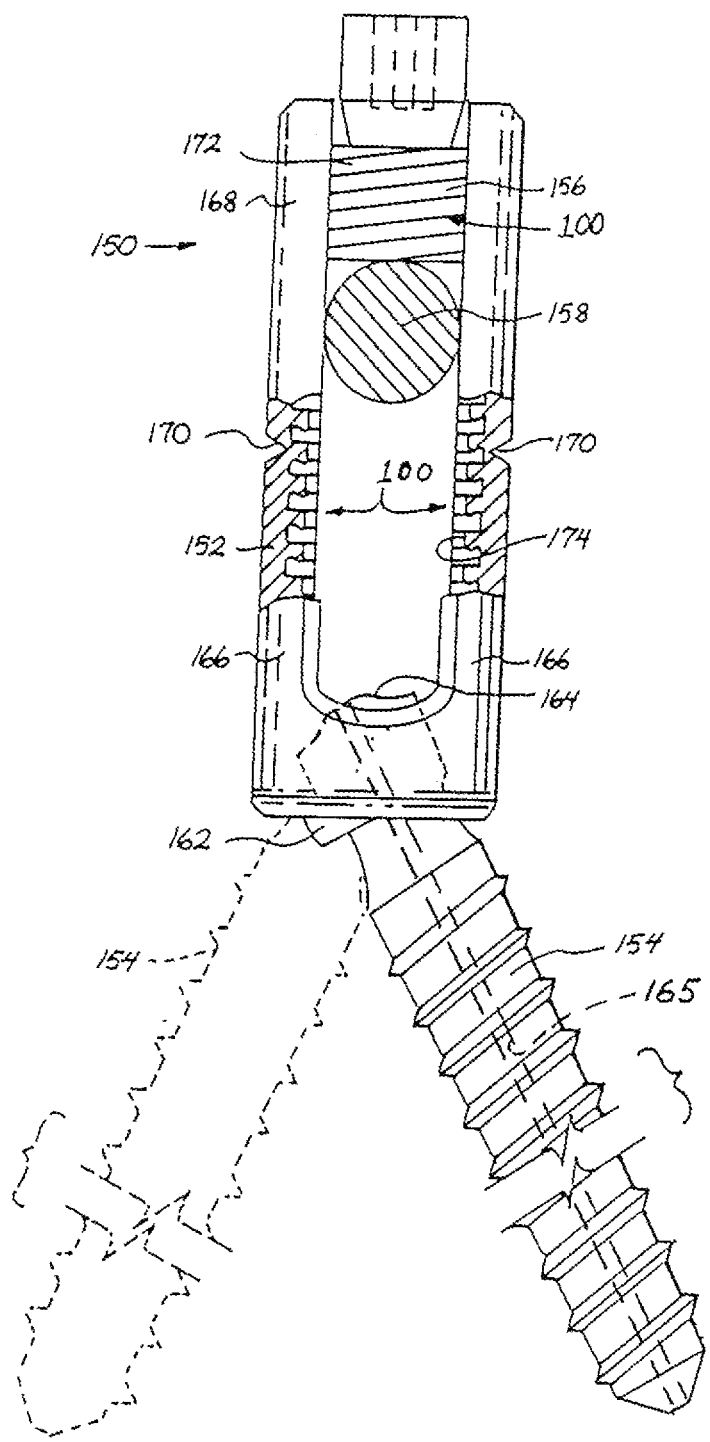
FIG. 6 is an enlarged fragmentary side elevational view of a spinal implant incorporating a helical guide and advancement flange of the present invention and including a polyaxial bone screw.

FIG. 6 illustrates a polyaxial medical implant, generally 150, that incorporates a helical guide and advancement flange structure 100 of the present invention identical to or substantially similar to the structure 1 previously described herein. The illustrated polyaxial implant 150 includes an open headed receiver 152, a threaded shank 154, and a closure 156 that cooperate to fix the position of another implant member, such as a spinal fixation rod 158. The receiver or head 152 is configured internally with a spherical socket (not shown) that receives a shank retainer member 162 having a spherical outer surface. The retainer member 162 is connected to an upper or capture end 164 of the shank 154 and, in cooperation with the receiver socket, enables the shank 154 to be positioned at any desired angle relative to the receiver 152, within a conical range of movement. The shank 154 is secured at the desired angle by engagement of the rod 158 with the upper or capture end 164 when the rod is clamped within the receiver 152 by the closure 156. Shown in phantom in the illustrated embodiment, the threaded shank 154 is cannulated, having a small central bore 165 extending an entire length of the shank body. The bore 165 provides a passage through the shank interior for a length of wire or pin inserted into a vertebra prior to the insertion of the threaded shank body 154, the wire or pin providing a guide for insertion of the shank 154 into the vertebra. Additional information about polyaxial bone screws can be found in U.S. Pat. No. 6,716,214, which is incorporated herein by reference.

The receiver 152 includes spaced apart arms 166 and preferably includes break-off extensions 168 that are separable from the arms 166 by breaking the extensions 168 off at weakened regions 170. The flange structure 100 includes an anti-splay closure guide and advancement flange 172 formed on the closure 156 which cooperates with a discontinuous receiver anti-splay guide and advancement flange 174 formed on inner surfaces of the arms 166 and extensions 168. The flanges 172 and 174 are substantially similar to the flanges 4 and 9 of the implant 3 and benefit from the same variations in configuration as described in connection therewith. The flanges 172 and 174 enable the closure 156 to be advanced into clamping contact with the rod 158 by rotation within the receiver 152. In other respects, the implant 150 is substantially similar to the implant 3.

It is to be understood that while certain forms of the present invention have been illustrated and described herein, it is not to be limited to the specific forms or arrangement of parts described and shown.

What is claimed and desired to be secured by Letters Patent is as follows:

1. In a device for securing a rod shaped member having a receiver with a pair of upwardly extended and spaced apart arms forming a rod receiving channel therebetween that receives a closure, the improvement comprising:
   a) the arms having main portions and extended portions connected to said main portions by weakened regions, said main portions and said extended portions of said arms having inner surfaces;
   b) a closure sized to be received within said channel to clamp the rod shaped member therein and having a body;
   c) a closure guide and advancement flange extending helically about and along said closure, said closure flange having a closure anti-splay contour with a downwardly facing closure leading surface and a trailing surface; the trailing surface having an inner portion extending outwardly and downwardly from the body and an outer portion that has a surface that is raised above the inner portion;
   d) a discontinuous receiver guide and advancement flange extending helically about and along said inner surfaces of said main portions and said extended portions of said arms, said receiver flange having a receiver anti-splay contour with an upwardly facing receiver leading surface; the closure trailing surface raised surface being sized and shaped to remain spaced from the receiver guide and advancement flange so as to remain unloaded during use;
   e) the anti-splay contours of said closure flange and said receiver flange being complementary to mate during rotation of the closure relative to the receiver, while radially interlocking, and thereafter cooperatively to prevent splaying of said arms when said closure is advanced into said receiver; said closure being advanceable against rod shaped member to clamp the member relative to said receiver; said downwardly facing closure leading surface and said upwardly facing receiver leading surface cooperating so as to produce a gap therebetween; and
   f) said extended portions of said arms guiding the closure into the channel during rotation of the closure into the channel and thereafter being separable from said main portions after said closure clamps the rod shaped member within a portion of said channel defined by said main portions of said arms.

2. The improvement as set forth in claim 1 wherein:
   a) said receiver is spinal fixation anchor and the rod shaped member is a spinal fixation rod.

3. The improvement as set forth in claim 1 wherein:
   a) said receiver is an open-headed bone screw adapted for implanting in a vertebra and said member is a spinal fixation rod.

4. The improvement as set forth in claim 1 wherein:
   a) said closure anti-splay contour includes a lip extending helically along said closure flange;
   b) said receiver anti-splay contour includes a groove extending helically along said receiver flange; and
   c) said lip and said groove cooperate to receive said lip in said groove when said closure is rotated and advanced into said receiver.

5. The improvement as set forth in claim 1 wherein:
   a) said closure flange has a closure load flank on a trailing side of said closure flange relative to a clamping direction of movement of said closure within said receiver;
   b) said closure anti-splay contour includes a lip extending helically along said closure load flank of said closure flange;
   c) said receiver flange has a receiver load flank on a trailing side of said receiver flange relative to said clamping direction of movement;
   d) said receiver anti-splay contour includes a groove extending helically along said receiver load flank of said receiver flange; and
   e) said lip and said groove cooperate to receive said lip in said groove when said closure is rotated and advanced into said receiver.

6. In a spinal fixation anchor for clamping and anchoring a spinal fixation rod having a an open head including a pair of spaced apart arms defining a rod receiving channel therebetween, the improvement comprising:
   a) the arms having main portions and extended portions connected to said main portions by weakened regions, said main portions and said extended portions of said arms having inner surfaces;
   b) a closure having a body and being sized to be received within said channel and adapted to be rotated and advanced into the channel and between the arms to clamp a spinal fixation rod in the channel;
   c) a closure guide and advancement flange extending helically about and along said closure, said closure flange having a closure anti-splay contour and a downwardly facing closure leading surface and a trailing surface; the trailing surface having an inner portion sloping downwardly and outwardly from the closure body and an outer portion with a raised surface;
   d) an anchor guide and advancement flange discontinuously extending helically about and along said inner surfaces of said main portions and said extended portions of said arms, said anchor flange having an anchor anti-splay contour and an upwardly facing anchor leading surface complementary to said closure leading surface; the closure trailing surface raised surface being sized and shaped so as to remain spaced from the anchor guide and advancement flange during use;
   e) an anti-splay gap between said complementary leading surfaces;
   f) the anti-splay contours of said closure flange and said anchor flange allowing rotation of the closure relative to the anchor while being complementary and radially interlocking so as to cooperate to prevent splaying of said arms when said closure is advanced into said anchor; and
   g) said extended portions of said arms being separable from said main portions after said closure clamps the rod within a portion of said channel between said main portions of said arms.

7. The improvement as set forth in claim 6 wherein:
 a) said anchor is an open-headed bone screw adapted for helical implanting in a vertebra.

8. The improvement as set forth in claim 6 wherein:
 a) said closure anti-splay contour includes a lip extending helically along said closure flange;
 b) said anchor anti-splay contour includes a groove extending helically along said receiver flange; and
 c) said lip and said groove cooperate to receive said lip in said groove when said closure is advanced into said anchor.

9. The improvement as set forth in claim 6 wherein:
 a) said closure flange has a closure load flank on a trailing side of said closure flange relative to a clamping direction of movement of said closure within said anchor;
 b) said closure anti-splay contour includes a lip extending helically along said closure load flank of said closure flange;
 c) said anchor flange has an anchor load flank on a trailing side of said anchor flange relative to said clamping direction of movement;
 d) said anchor anti-splay contour includes a groove extending helically along said anchor load flank of said anchor flange; and
 e) said lip and said groove cooperate to receive said lip in said groove when said closure is advanced into said anchor.

10. In a spinal fixation bone screw for clamping and anchoring a spinal fixation rod having a an open head including a pair of spaced apart arms defining a rod receiving channel therebetween,
the improvement comprising:
 a) the arms having main portions and extended portions connected to said main portions by weakened regions, said main portions and said extended portions of said arms having inner surfaces;
 b) a closure having a body and being sized to be received within said channel to clamp a spinal fixation rod therein;
 c) a closure guide and advancement flange extending helically about and along said closure, said closure flange having a closure anti-splay contour with a downwardly facing closure leading surface and a trailing surface, the trailing surface having an inner portion that slopes outwardly and downwardly from the body and an outer portion with a raised surface relative to the inner portion;
 d) a head guide and advancement flange discontinuously extending helically about and along said inner surfaces of said main portions and said extended portions of said arms, said head flange having a head anti-splay contour with an upwardly facing head leading surface;
 e) the anti-splay contours of said closure flange and said head flange being complementary and radially interlocking so as to cooperate to prevent splaying of said arms when said flanges are mated and said closure is rotated and advanced into said screw head with the head flange mating with the closure flange between the arm extended portions and guiding the closure into the channel between the arm main portions; the trailing surface raised surface being sized and shaped to be spaced from the head guide and advancement flange during use;
 f) the closure leading surface and the head leading surface cooperating when said flanges are mated and said closure is rotated and advanced into said screw head with the head flange mating with the closure flange between the arm extended portions and guiding the closure into the channel between the arm main portions; and
 g) said extended portions of said arms being separated from said main portions after said closure clamps the rod within a portion of said channel located between said main portions of said arms.

11. The improvement as set forth in claim 10 wherein:
 a) said closure anti-splay contour includes a lip extending helically along said closure flange;
 b) said head anti-splay contour includes a groove extending helically along said head flange; and
 c) said lip and said groove cooperate to receive said lip in said groove when said closure is advanced into said screw head.

12. The improvement as set forth in claim 10 wherein:
 a) said closure flange has a closure load flank on a trailing side of said closure flange relative to a clamping direction of movement of said closure within said screw head;
 b) said closure anti-splay contour includes a lip extending helically along said closure load flank of said closure flange;
 c) said head flange has a head load flank on a trailing side of said head flange relative to said clamping direction of movement;
 d) said anchor anti-splay contour includes a groove extending helically along said anchor load flank of said head flange; and
 e) said lip and said groove cooperate to receive said lip in said groove when said closure is advanced into said head.

13. The improvement as set forth in claim 10 wherein:
 a) said closure includes a break off insertion head adapted to be driven by an insertion tool and to break off at a preselected torque.

14. The improvement as set forth in claim 10 wherein:
 a) said bone screw is a polyaxial bone screw.

15. The improvement as set forth in claim 10 wherein:
 a) said bone screw is a fixed headed bone screw.

16. In a device for securing a rod shaped member having a receiver with a pair of upwardly extended and spaced apart arms forming a rod receiving channel therebetween that receives a closure, the improvement comprising:
 a) said arms have upwardly extending break off extensions;
 b) the closure has a body and a flange form thereabout with a trailing surface;
 c) said arms and said extensions each have inwardly facing surfaces with discontinuous helically wound flange forms thereon that interlock with the flange form on the closure and allow advancement and transfer of the closure between said extensions and said arms by rotation of the closure; wherein
 d) the closure includes leading and trailing surfaces; the closure trailing surface having an inner portion sloping downwardly from the body and an outer portion with a raised surface forming a lip that remains spaced from the flange forms of the arms and extensions so as to remain unloaded when the flange forms are mated and said closure is rotated and advanced into said screw head and tightened.

17. The improvement as set forth in claim 16, wherein:
 a) said receiver is an open-headed bone screw adapted for implanting in a vertebra and said member is a spinal fixation rod.

18. In a device for securing a rod shaped member having a receiver with a pair of upwardly extended and spaced apart arms forming a rod receiving channel therebetween that receives a closure, the improvement comprising:
 a) the arms having main portions and extended portions connected to said main portions by weakened regions, said main portions and said extended portions of said arms having inner surfaces;

b) a closure with a body and sized to be received within said channel to clamp the rod shaped member therein;

c) a closure guide and advancement flange extending helically about and along said closure body, said closure flange having a closure anti-splay contour with an inner portion that slopes downwardly and outwardly from the body and an outer portion with a raised surface relative to the inner portion; the outer portion raised surface remaining unloaded in use;

d) a discontinuous receiver guide and advancement flange extending helically about and along said inner surfaces of said main portions and said extended portions of said arms, said receiver flange having a mating receiver anti-splay contour;

e) the anti-splay contours of said closure flange and said receiver flange being complementary to mate during rotation of the closure relative to the receiver, while radially interlocking, and thereafter cooperatively to prevent splaying of said arms when said closure is advanced into said receiver; said closure being advanceable to lock rod shaped member to said receiver; and f) said extended portions of said arms guiding the closure into the channel during rotation of the closure into the channel and thereafter being separable from said main portions after said closure clamps the rod shaped member within a portion of said channel defined by said main portions of said arms.

19. In a device for securing a rod shaped member having a receiver with a pair of upwardly extended and spaced apart arms forming a rod receiving channel therebetween that receives a closure, the improvement comprising:

a) the closure has a body and a flange form thereabout with a trailing surface;

b) said arms have inwardly facing surfaces with discontinuous helically wound flange forms thereon that interlock with the flange form on the closure and allow advancement of the closure along said arms by rotation of the closure; wherein c) the closure includes leading and trailing surfaces; the extending outwardly and trailing surface having an inner portion sloping downwardly from the body and an outer portion with a raised surface forming a lip that remains spaced from the flange forms of the arms so as to remain unloaded when the closure and arm flange forms are mated and the closure is rotated and advanced into the screw head and tightened.

20. The improvement as set forth in claim 19, wherein:

a) said receiver is an open-headed bone screw adapted for implanting in a vertebra and said member is a spinal fixation rod.

21. A device for securing a rod shaped member having a receiver with a pair of upwardly extended and spaced apart arms forming a rod receiving channel therebetween that receives a closure, the improvement comprising:

a) the arms having inner surfaces;

b) a closure sized to be received within said channel to clamp the rod shaped member therein and having a body;

c) a closure guide and advancement flange extending helically about and along the closure, the closure flange having a closure anti-splay contour with a downwardly facing closure leading surface and a trailing surface; the trailing surface having an inner portion extending outwardly and downwardly from the body and an outer portion that has a surface that is raised above the inner portion;

d) a discontinuous receiver guide and advancement flange extending helically about and along the inner surfaces of the arms, the receiver flange having a receiver anti-splay contour with an upwardly facing receiver leading surface; the closure trailing surface raised surface being sized and shaped to remain spaced from the receiver guide and advancement flange so as to remain unloaded during use; and e) the anti-splay contours of said closure flange and said receiver flange being complementary to mate during rotation of the closure relative to the receiver, while radially interlocking, and thereafter cooperate to resist splaying of said arms when said closure is advanced into the receiver; the closure being advanceable against rod shaped member to clamp and secure the member relative to said receiver; the downwardly facing closure leading surface and said upwardly facing receiver leading surface being sized and shaped so as to produce a gap therebetween during use.

* * * * *